(12) United States Patent
Ono

(10) Patent No.: US 10,595,389 B2
(45) Date of Patent: Mar. 17, 2020

(54) X-RAY HIGH VOLTAGE GENERATOR, X-RAY IMAGING APPARATUS, ASSESSING CIRCUIT, AND MEDICAL POWER SUPPLY DEVICE

(71) Applicant: Canon Medical Systems Corporation, Otawara-shi (JP)

(72) Inventor: Masahiko Ono, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 111 days.

(21) Appl. No.: 15/994,130

(22) Filed: May 31, 2018

(65) Prior Publication Data

US 2018/0352640 A1 Dec. 6, 2018

(30) Foreign Application Priority Data

Jun. 1, 2017 (JP) .................. 2017-109523

(51) Int. Cl.
*H05G 1/54* (2006.01)
*H05G 1/46* (2006.01)
(Continued)

(52) U.S. Cl.
CPC .................. *H05G 1/54* (2013.01); *A61B 6/03* (2013.01); *A61B 6/032* (2013.01); *A61B 6/40* (2013.01); *A61B 6/405* (2013.01); *A61B 6/4441* (2013.01); *A61B 6/54* (2013.01); *A61B 6/56* (2013.01); *A61B 6/563* (2013.01); *A61B 6/586* (2013.01); *H01L 23/34* (2013.01);
(Continued)

(58) Field of Classification Search
CPC .. H05G 1/54; H05G 1/10; H05G 1/32; H05G 1/38; H05G 1/46; A61B 6/03; A61B 6/032; A61B 6/40; A61B 6/405; A61B 6/4441; A61B 6/54; A61B 6/56; A61B 6/563; A61B 6/586; A61B 6/10; H01L 23/34; H02M 3/33569
USPC .................................. 378/101–118
See application file for complete search history.

(56) References Cited

U.S. PATENT DOCUMENTS 4,589,501 A * 5/1986 Arya ................... E21D 21/0093
173/131
4,597,026 A * 6/1986 Santurtun ........... H02M 3/3376
361/100
(Continued)

FOREIGN PATENT DOCUMENTS

| JP | 2011-23569  | 2/2011 |
|----|-------------|--------|
| JP | 2013-142704 | 7/2013 |
| JP | 2014-56668  | 3/2014 |

*Primary Examiner* — Courtney D Thomas
(74) *Attorney, Agent, or Firm* — Oblon, McClelland, Maier & Neustadt, L.L.P.

(57) ABSTRACT

An X-ray high voltage generator according to an embodiment includes an inverter circuit, a power device, a Pulse Width Modulation (PWM) circuit, and processing circuitry. The inverter circuit is configured to control output voltage to be output to an X-ray tube configured to generate an X-ray. The power device is provided for the inverter circuit and is configured to perform a switching process to control the output voltage. The PWM circuit is configured to control the switching process performed by the power device on the basis of an ON time period, in accordance with the output voltage. The processing circuitry is configured to output information about a product life of the power device on the basis of the ON time period.

11 Claims, 7 Drawing Sheets

(51) Int. Cl.
*H05G 1/32* (2006.01)
*H05G 1/10* (2006.01)
*H01L 23/34* (2006.01)
*A61B 6/03* (2006.01)
*A61B 6/00* (2006.01)
*H05G 1/38* (2006.01)
*H02M 3/335* (2006.01)
*H05G 1/22* (2006.01)
*A61B 6/10* (2006.01)

(52) U.S. Cl.
CPC .......... *H02M 3/33569* (2013.01); *H05G 1/10* (2013.01); *H05G 1/22* (2013.01); *H05G 1/32* (2013.01); *H05G 1/38* (2013.01); *H05G 1/46* (2013.01); *A61B 6/10* (2013.01)

(56) References Cited

U.S. PATENT DOCUMENTS

| | | | |
|---|---|---|---|
| 7,233,645 B2 * | 6/2007 | Feda | G01N 23/223 378/102 |
| 2013/0177041 A1 | 7/2013 | Sundaramoorthy et al. | |
| 2014/0233708 A1 | 8/2014 | Ishiyama et al. | |

* cited by examiner

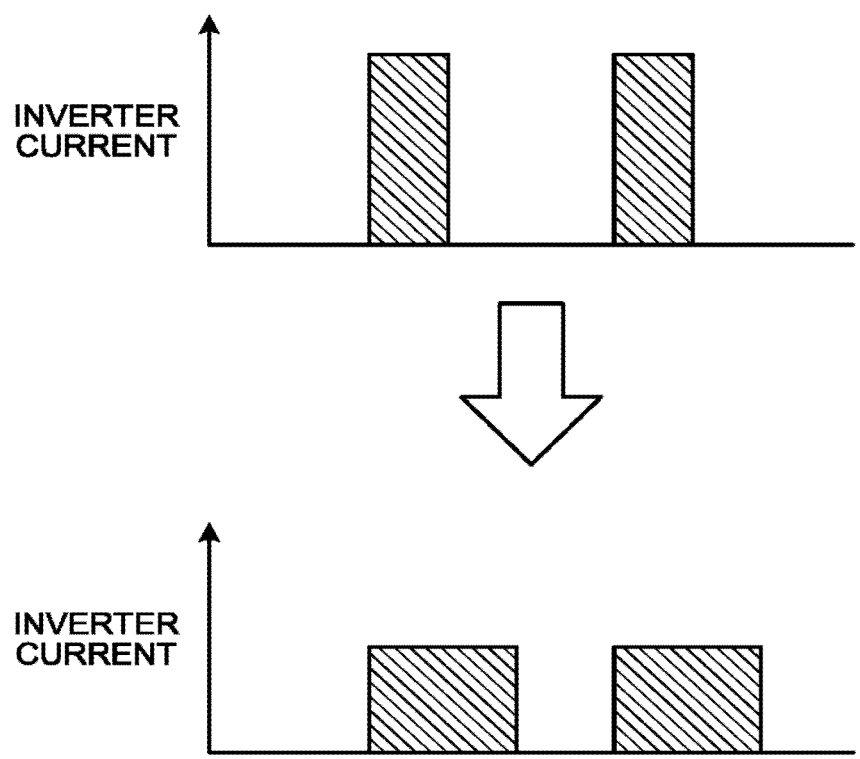

FIG.8
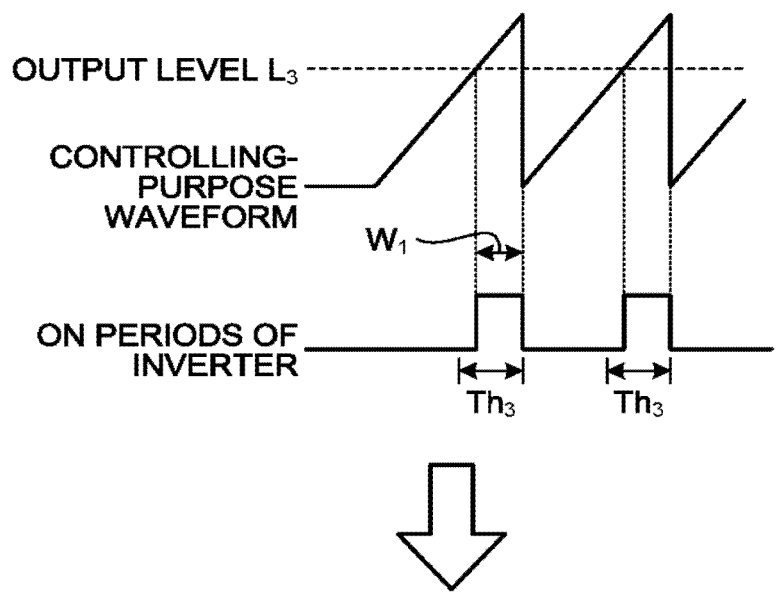
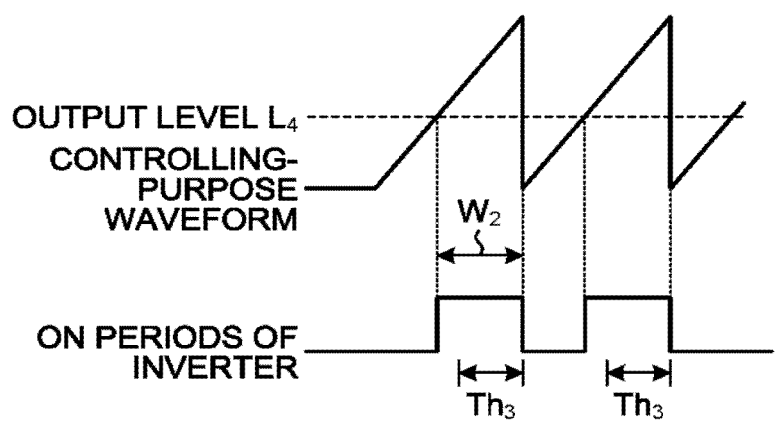

X-RAY HIGH VOLTAGE GENERATOR, X-RAY IMAGING APPARATUS, ASSESSING CIRCUIT, AND MEDICAL POWER SUPPLY DEVICE

CROSS-REFERENCE TO RELATED APPLICATIONS

This application is based upon and claims the benefit of priority from Japanese Patent Application No. 2017-109523, filed on Jun. 1, 2017; the entire contents of which are incorporated herein by reference.

FIELD

Embodiments described herein generally relate to an X-ray high voltage generator, an X-ray imaging apparatus, an assessing circuit, and a medical power supply device.

BACKGROUND

Conventionally, in X-ray diagnosis apparatuses and X-ray Computed Tomography (CT) apparatuses, an X-ray high voltage generator is used for the purpose of supplying high voltage to an X-ray tube. The X-ray high voltage generator is, generally speaking, a high voltage power supply in which an inverter circuit, a high voltage transformer, a rectifying circuit, and the like are combined together.

Examples of a switching device provided for the inverter circuit include, generally speaking, a power device (a power element) such as an Insulated Gate Bipolar Transistor (IGBT) or a Metal-Oxide-Semiconductor Field-Effect Transistor (MOS-FET). Because a large current flows through the inverter circuit, the power device is worn out (deteriorated) through repeated use and will eventually be damaged. For this reason, for example, a device configured to monitor changes in the temperature of the power device and to estimate the product life of the power device or a device that realizes redundancy by using a plurality of inverter circuits have been proposed.

BRIEF DESCRIPTION OF THE DRAWINGS

FIG. 6 is yet another drawing for explaining the PWM control exercised by the PWM circuit;

FIG. 7 is a drawing for explaining a process performed by a product life assessing circuit according to the first embodiment;

FIG. 8 is another drawing for explaining the process performed by the product life assessing circuit according to the first embodiment;

DETAILED DESCRIPTION

An object to be achieved by the present disclosure is to properly assess expiration of the product life (hereinafter, simply "product life") of a power device.

An X-ray high voltage generator according to an embodiment includes an inverter circuit, a power device, a Pulse Width Modulation (PWM) circuit, and processing circuitry. The inverter circuit is configured to control output voltage to be output to an X-ray tube configured to generate an X-ray. The power device is provided for the inverter circuit and is configured to perform a switching process to control the output voltage. The PWM circuit is configured to control the switching process performed by the power device on the basis of ON time periods (hereinafter "ON periods"), in accordance with the output voltage. The processing circuitry is configured to output information about the product life of the power device on the basis of an ON period.

In the following sections, exemplary embodiments of an X-ray high voltage generator, an X-ray imaging apparatus, an assessing circuit, and a medical power supply device will be explained, with reference to the accompanying drawings. Possible embodiments are not limited to the embodiments described below. Further, the contents of each of the embodiments are, in principle, similarly applicable to any other embodiment.

The term "X-ray imaging apparatus" is a generic term for medical image diagnosis apparatuses in which an X-ray tube is installed and may be, for example, an X-ray diagnosis apparatus or an X-ray CT apparatus. In the embodiments described below, examples will be explained in which the present disclosure is applied to an X-ray diagnosis apparatus; however, the present disclosure is similarly applicable to an X-ray CT apparatus.

First Embodiment

Figure 1:
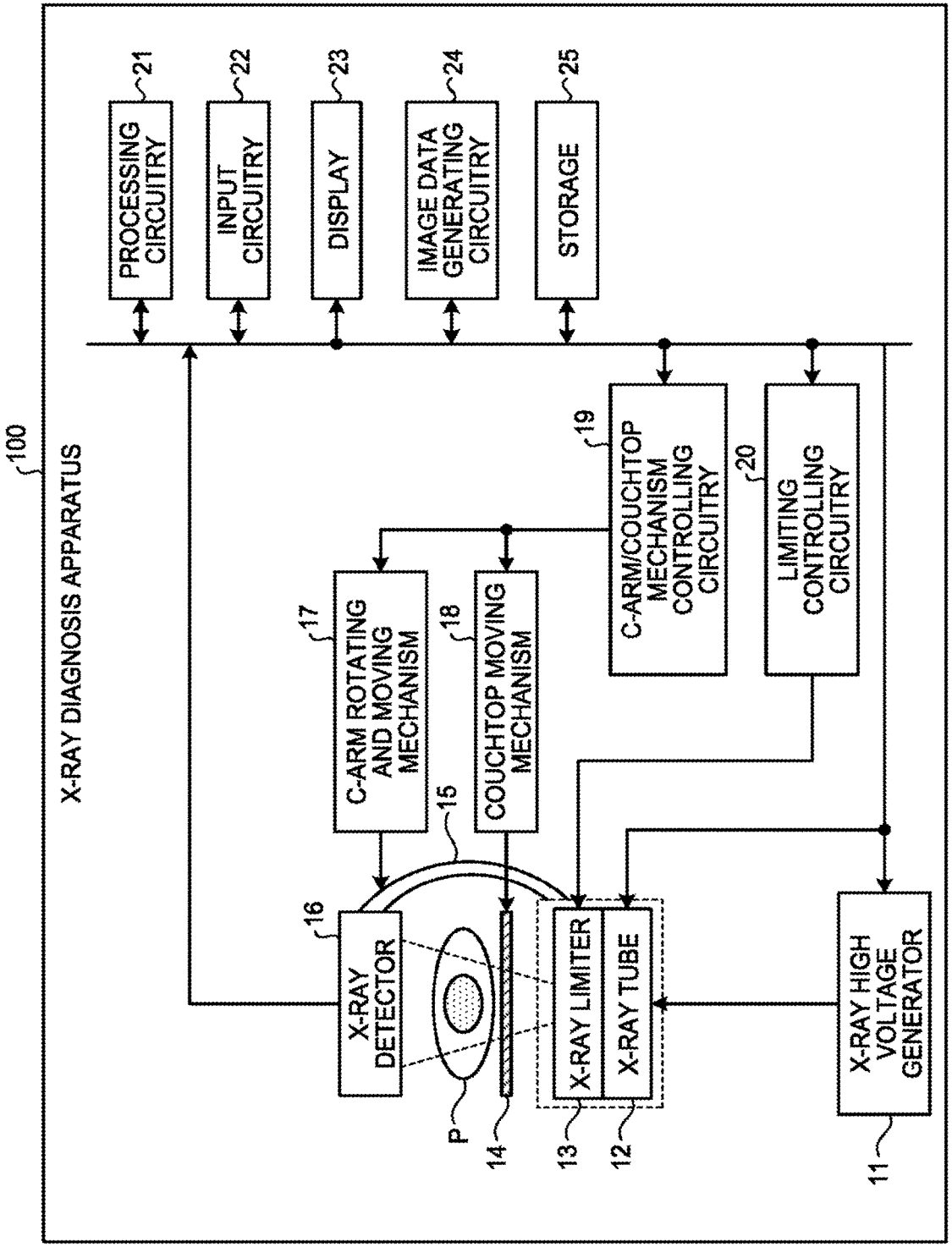
FIG. 1 is a block diagram illustrating an exemplary configuration of an X-ray diagnosis apparatus according to a first embodiment.

To begin with, an exemplary configuration of an X-ray diagnosis apparatus 100 according to a first embodiment will be explained with reference to FIG. 1. FIG. 1 is a block diagram illustrating the exemplary configuration of the X-ray diagnosis apparatus 100 according to the first embodiment.

As illustrated in FIG. 1, the X-ray diagnosis apparatus 100 includes an X-ray high voltage generator 11, an X-ray tube 12, an X-ray limiter 13, a couchtop 14, a C-arm 15, and an X-ray detector 16. Further, the X-ray diagnosis apparatus 100 includes a C-arm rotating and moving mechanism 17, a couchtop moving mechanism 18, C-arm/couchtop mechanism controlling circuitry 19, and limiting controlling circuitry 20. Further, the X-ray diagnosis apparatus 100 includes processing circuitry 21, input circuitry 22, a display 23, image data generating circuitry 24, and storage 25.

The X-ray high voltage generator 11 is a high voltage power supply configured, under control of the processing circuitry 21, to generate high voltage and to supply the generated high voltage to the X-ray tube 12. For example, the X-ray high voltage generator 11 may be structured with an inverter circuit, a high voltage transformer that generates the high voltage, a high voltage rectifying circuit, and the like. The X-ray high voltage generator 11 is configured to control the output voltage output from the X-ray high voltage generator 11 to the X-ray tube 12, by varying ON periods (an ON cycle) of a switching device in the inverter circuit. Examples of the switching device provided for the inverter circuit include, generally speaking, a power device (a power element) such as an Insulated Gate Bipolar Transistor (IGBT) or a Metal-Oxide-Semiconductor Field-Effect Transistor (MOS-FET). The X-ray high voltage generator 11 is an example of an X-ray high voltage device.

The X-ray tube 12 is a device configured to generate X-rays by using the high voltage supplied thereto from the X-ray high voltage generator 11. The X-ray tube 12 is structured with a vacuum tube that receives the supply of the high voltage from the X-ray high voltage generator 11 and emits thermo electrons from a negative pole (a filament) to a positive pole (a target).

The X-ray limiter 13 is a member configured to limit the X-rays generated by the X-ray tube 12 so as to be selectively radiated onto an imaging target region of the patient P, under control of the limiting controlling circuitry 20. For example, the X-ray limiter 13 is structured with limiting blades and a filter. The limiting blades may be, for example, four plate-like slidable members. As being slid by the limiting controlling circuitry 20, the limiting blades are configured to limit the X-rays generated by the X-ray tube 12. Further, the filter is an X-ray filter used for adjusting (attenuating) the X-rays radiated onto the patient P. For example, the filter is configured to adjust the X-rays generated by the X-ray tube 12, by changing the radiation quality of the X-rays passing therethrough with the material and/or the thickness thereof.

The couchtop 14 is a bed on which the patient P is placed and is arranged over a couch (not illustrated). It should be noted that the patient P is not included in the X-ray diagnosis apparatus 100. The X-ray detector 16 includes detecting elements arranged in a matrix formation and is configured to detect X-rays that have passed through the patient P. For example, the X-ray detector 16 includes, as the detecting elements, Complementary Metal Oxide Semiconductor (CMOS) elements or Charge Coupled Devices (CCDs). The detecting elements are configured to convert the X-rays that have passed through the patient P into electrical signals, to accumulate the electrical signals therein, and to transmit the accumulated electrical signals to the image data generating circuitry 24.

The C-arm 15 is a supporting member configured to support the X-ray tube 12, the X-ray limiter 13, and the X-ray detector 16. The X-ray tube 12 with the X-ray limiter 13 and the X-ray detector 16 are arranged by the C-arm 15 so as to oppose each other while the patient P is interposed therebetween.

The C-arm rotating and moving mechanism 17 is a motive power mechanism used for rotating and moving the C-arm 15. For example, the C-arm rotating and moving mechanism 17 is configured to rotate and move the C-arm 15 by using motive power generated by an actuator such as a motor or the like. Further, the couchtop moving mechanism 18 is a motive power mechanism used for moving the couchtop 14. For example, the couchtop moving mechanism 18 is configured to move the couchtop 14 by using motive power generated by an actuator.

The C-arm/couchtop mechanism controlling circuitry 19 is an electronic circuit configured to control the C-arm rotating and moving mechanism 17 and the couchtop moving mechanism 18, under the control of the processing circuitry 21. For example, by controlling the C-arm rotating and moving mechanism 17 and the couchtop moving mechanism 18, the C-arm/couchtop mechanism controlling circuitry 19 adjusts the rotating and the moving of the C-arm 15 and the moving of the couchtop 14.

The limiting controlling circuitry 20 is an electronic circuit configured to control operations of the X-ray limiter 13, under the control of the processing circuitry 21. For example, the limiting controlling circuitry 20 is configured to control the radiation range of the X-rays radiated onto the patient P, by sliding the limiting blades included in the X-ray limiter 13. Further, the limiting controlling circuitry 20 is configured to control the distribution of the dose of the X-rays radiated onto the patient P, by adjusting the position of the filter included in the X-ray limiter 13.

The image data generating circuitry 24 is an electronic circuit configured to generate image data. For example, the image data generating circuitry 24 is configured to generate the image data by using the electrical signals converted from the X-rays by the X-ray detector 16 and to store the generated image data into the storage 25. For example, the image data generating circuitry 24 generates the image data by applying a current/voltage conversion, an Analog/Digital (AD) conversion, and/or a parallel/serial conversion to the electrical signals received from the X-ray detector 16. Further, the image data generating circuitry 24 stores the generated image data into the storage 25.

The storage 25 is a storage device configured to receive and store therein the image data generated by the image data generating circuitry 24. The storage 25 is also configured to store therein the image data resulting from a filtering process performed by the processing circuitry 21 (explained later). Further, the storage 25 is configured to stores therein computer programs (hereinafter, "programs") corresponding to various types of functions that are read and executed by the circuits illustrated in FIG. 1.

The input circuitry 22 is realized with a trackball, a switch button, a mouse, a keyboard, and/or the like used for issuing various types of instructions and establishing various types of settings. The input circuitry 22 is connected to the processing circuitry 21 and is configured to convert an input operation received from the operator into an electrical signal and to output the electrical signal to the processing circuitry 21. The display 23 is a display device configured to display a Graphical User Interface (GUI) used for receiving instructions from the operator, as well as X-ray images. For example, the display 23 displays an X-rays image resulting from the filtering process performed by the processing circuitry 21.

The processing circuitry 21 is electronic circuitry configured to control operations of the entirety of the X-ray diagnosis apparatus 100. For example, the processing circuitry 21 controls the dose and the turning off and on of the X-rays radiated onto the patient P, by controlling the X-ray high voltage generator 11 according to an instruction from the operator transferred thereto from the input circuitry 22 so as to adjust the voltage supplied to the X-ray tube 12. Further, for example, the processing circuitry 21 controls the C-arm/couchtop mechanism controlling circuitry 19 according to an instruction from the operator so as to adjust the rotating and the moving of the C-arm 15 and the moving of the couchtop 14. Further, the processing circuitry 21 controls the distribution of the dose of the X-rays by controlling the limiting controlling circuitry 20. Further, by controlling the image data generating circuitry 24, the processing circuitry 21 acquires the image data by controlling the image data generating process based on the electrical signals converted from the X-rays by the X-ray detector 16. Further, the processing circuitry 21 causes the display 23 to display the X-ray image resulting from the filtering process and causes the display 23 to display the GUI used for receiving instructions from the operator.

In the X-ray diagnosis apparatus 100 illustrated in FIG. 1, processing functions thereof are stored in the storage 25 in the form of computer-executable programs. For example, the C-arm/couchtop mechanism controlling circuitry 19, the limiting controlling circuitry 20, the processing circuitry 21, and the image data generating circuitry 24 are processors configured to realize the functions corresponding to the programs by reading and executing the programs from the storage 25. In other words, each of the circuits that has read the corresponding one of the programs has the function corresponding to the read program.

The term "processor" used in the explanation above denotes, for example, a circuit such as a Central Processing Unit (CPU), a Graphics Processing Unit (GPU), an Application Specific Integrated Circuit (ASIC), a programmable logic medical device (e.g., a Simple Programmable Logic medical Device [SPLD], a Complex Programmable Logic medical Device [CPLD]), or a Field Programmable Gate Array (FPGA). Each of the processors realizes the functions thereof by reading and executing a corresponding one of the programs stored in the storage 25. Alternatively, it is also acceptable to directly incorporate the program into a circuit of each of the processors, instead of having the programs stored in the storage 25. In that situation, each of the processors realizes the functions thereof by reading and executing the program incorporated in the circuit thereof. Each of the processors described in the present embodiments does not necessarily have to be configured as a single circuit individually. For instance, a plurality of independent circuits may be combined together to structure a single processor so as to realize the functions thereof.

Incidentally, because a large current flows through the inverter circuit within the X-ray high voltage generator 11, the power device is worn out (deteriorated) through repeated use and will eventually be damaged. When the power device is damaged, it will not be possible for the X-ray high voltage generator 11 to output high voltage. In other words, the X-ray diagnosis apparatus 100 will not be able to output X-rays, which means that it is impossible to perform an image diagnosis process. In particular, when the power device gets damaged during an angiography process or the like, the user will not be able to continue manipulations, and the medical examination will be disrupted to a large extent.

To cope with this situation, the X-ray diagnosis apparatus 100 according to the present embodiment is provided with the configuration explained below, for the purpose of properly assessing the product life of the power device. Next, the X-ray diagnosis apparatus 100 according to the present embodiment will be explained in detail, with reference to the accompanying drawings.

Figure 2:
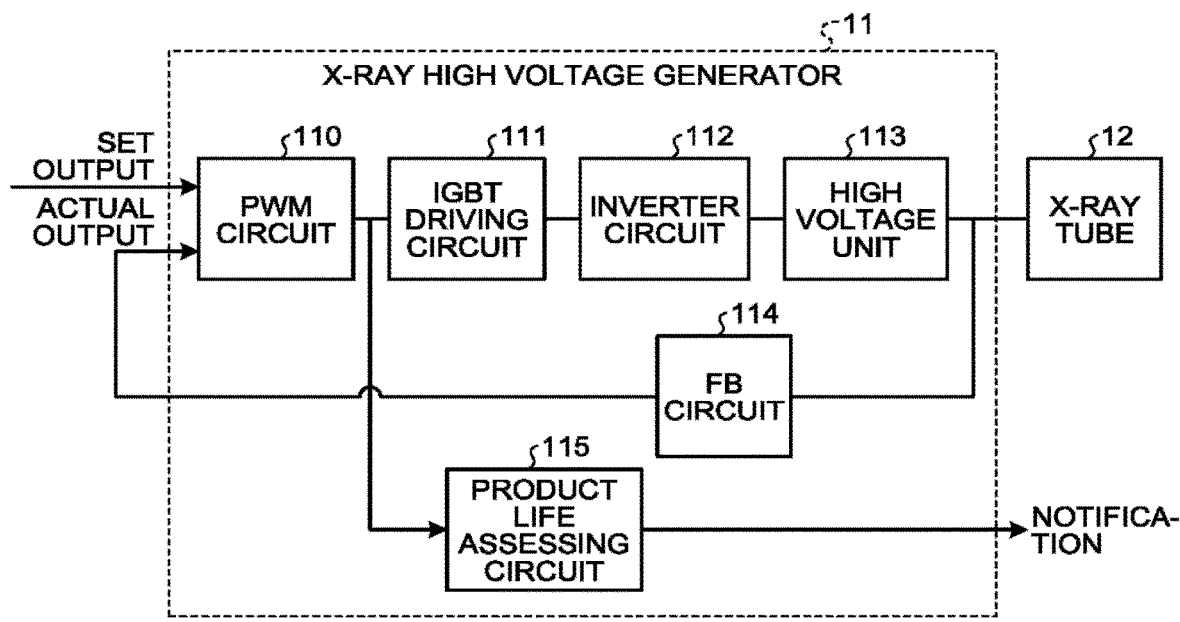
FIG. 2 is a block diagram illustrating an exemplary configuration of an X-ray high voltage generator according to the first embodiment.
Figure 3:
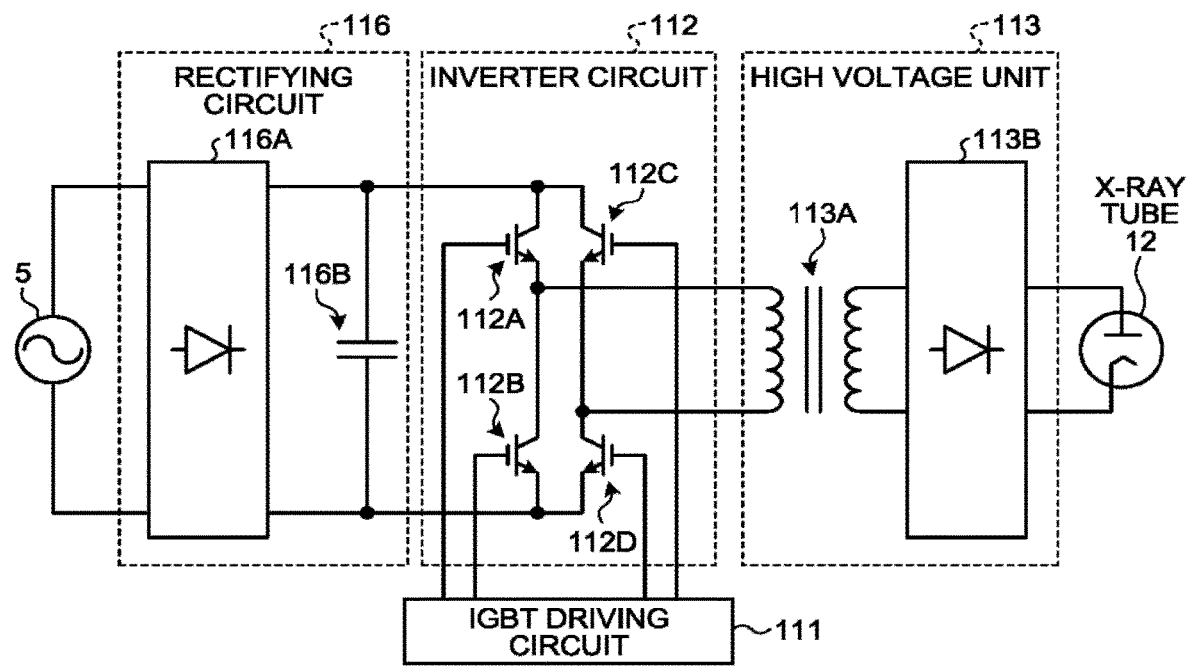
FIG. 3 is a block diagram illustrating another exemplary configuration of the X-ray high voltage generator according to the first embodiment.

An exemplary configuration of the X-ray high voltage generator 11 according to the first embodiment will be explained, with reference to FIGS. 2 and 3. FIGS. 2 and 3 are block diagrams illustrating exemplary configurations of the X-ray high voltage generator 11 according to the first embodiment.

As illustrated in FIG. 2, the X-ray high voltage generator 11 includes a Power Width Modulation (PWM) circuit 110, an IGBT driving circuit 111, an inverter circuit 112, a high voltage unit 113, a feedback (FB) circuit 114, and a product life assessing circuit 115.

Generally speaking, PWM control is a method for controlling output voltage by repeatedly switching a power device on and off. When PWM control is exercised, it is possible to obtain an arbitrary output voltage level by adjusting the pulse width corresponding to a time period of the ON state (an ON period), in accordance with a result of a comparison between an input value and a reference value to be compared therewith.

The PWM circuit 110 according to the present embodiment is configured to control (to exercise PWM control over) the output of the X-ray high voltage generator by varying the switching time period (the ON period) of a power device (IGBTs 112A to 112D explained below). For example, the PWM circuit 110 generates a pulse signal having a cycle that indicates switching timing of the inverter circuit 112. The pulse signal has a pulse width (an ON period) corresponding to the time period during which the inverter circuit 112 is in an ON state. In other words, the PWM circuit 110 is configured to generate a pulse signal of which the pulse width is varied in accordance with a desired voltage level. The PWM circuit 110 outputs the generated pulse signal to the IGBT driving circuit 111.

The IGBT driving circuit 111 is a circuit used for driving the IGBTs in accordance with the output of the PWM circuit 110. The IGBT driving circuit 111 is configured to switch the IGBTs 112A to 112D on and off, by controlling the voltage applied to gate electrodes of the IGBTs 112A to 112D.

More specifically, the IGBT driving circuit 111 receives the pulse signal of which the ON periods (the pulse width) are controlled by the PWM circuit 110. Further, the IGBT driving circuit 111 switches the IGBTs 112A to 112D on and off by switching the voltage applied to the gate electrodes of the IGBTs 112A to 112D, with the timing based on the pulse width of the received pulse signal.

The inverter circuit 112 is an electronic circuit configured to control the output voltage to be output to the X-ray tube 12 that generates X-rays. The high voltage unit 113 is an electronic circuit configured to generate the output voltage to be output to the X-ray tube 12.

With reference to FIG. 3, exemplary configurations of the inverter circuit 112 and the high voltage unit 113 will be explained. As illustrated in FIG. 3, the inverter circuit 112 includes the four IGBTs 112A, 112B, 112C, and 112D. Further, the high voltage unit 113 includes a high voltage transformer 113A and an AC/DC converter 113B. Further, the inverter circuit 112 is connected to a rectifying circuit 116. The rectifying circuit 116 includes an AC/DC converter 116A and a smoothing capacitor 116B. The rectifying circuit 116 is connected to a power supply 5. In this situation, the IGBTs 112A, 112B, 112C, and 112D represent an example of the power device.

The power supply 5 is, for example, a commercial power supply configured to supply alternating-current voltage. The alternating-current voltage supplied by the power supply 5 is converted into direct-current voltage by the AC/DC converter 116A, smoothed by the smoothing capacitor 116B, and subsequently supplied to the inverter circuit 112.

For example, the inverter circuit 112 converts the direct-current voltage resulting from the conversion by the AC/DC converter 116A into alternating-current voltage having a predetermined frequency. For example, under the control of the IGBT driving circuit 111, in the inverter circuit 112, the IGBT 112A and the IGBT 112B turn on and off alternately, whereas the IGBT 112C and the IGBT 112D turn on and off alternately. In this situation, the inverter circuit 112 is controlled so that the timing with which the IGBT 112A and the IGBT 112D turn on and off is in synchronization with each other and so that the timing with which the IGBT 112B and the IGBT 112C turn on and off is in synchronization with each other. Accordingly, the inverter circuit 112 converts the direct-current voltage smoothed by the smoothing capacitor 116B into alternating-current voltage having a high frequency.

More specifically, when the IGBT 112A and the IGBT 112D are on, the current flows to the high voltage transformer 113A via the IGBT 112A so as to flow into the IGBT 112D. In contrast, when the IGBT 112B and the IGBT 112C are on, the current flows to the high voltage transformer 113A via the IGBT 112C so as to flow into the IGBT 112B.

In other words, the inverter circuit 112 is configured so that, among the four IGBTs 112A, 112B, 112C, and 112D, the IGBT 112A and the IGBT 112D work as one pair (which may hereinafter be referred to as "pair A"), whereas the IGBT 112B and the IGBT 112C work as another pair (which may hereinafter be referred to as "pair B"), so that the two pairs are turned on and off alternately.

With this arrangement, with respect to the high voltage transformer 113A, the current flows in the opposite direction between when the pair A (the IGBT 112A and the IGBT 112D) is turned on and when the pair B (the IGBT 112B and the IGBT 112C) is turned on, so that the alternating-current voltage is supplied thereto. Further, the frequency of the alternating-current voltage supplied to the high voltage transformer 113A is controlled by the switching speed of the IGBTs 112A, 112B, 112C, and 112D.

For example, the high voltage unit 113 is a device configured to generate the direct-current high voltage by increasing the voltage level and rectifying the alternating-current voltage that was generated by the inverter circuit 112 and has a predetermined frequency. For example, the high voltage transformer 113A increases the level of the alternating-current voltage supplied from the inverter circuit 112. After that, the AC/DC converter 113B converts the alternating-current voltage of which the level was increased by the high voltage transformer 113A, into direct-current voltage and supplies the direct-current voltage to the X-ray tube 12.

Returning to the description of FIG. 2, the Feedback (FB) circuit 114 is an electric circuit configured to divide the voltage output from the high voltage unit 113 and to output the divided voltage to the PWM circuit 110. For example, the FB circuit 114 is structured with a resistor, so as to lower the level of the output voltage output from the high voltage unit 113 and to output the lowered voltage to the PWM circuit 110. In this situation, a signal output from the FB circuit 114 to the PWM circuit 110 has a voltage level corresponding to the level of the output voltage. In other words, the FB circuit 114 outputs the signal corresponding to the level of the output voltage (the actual output), to the PWM circuit 110.

After that, when having received, from the FB circuit 114, an input of the signal corresponding to the level of the output voltage (the actual output), the PWM circuit 110 compares the actual output with a set voltage level and controls the ON periods in accordance with the result of the comparison.

Figure 4:
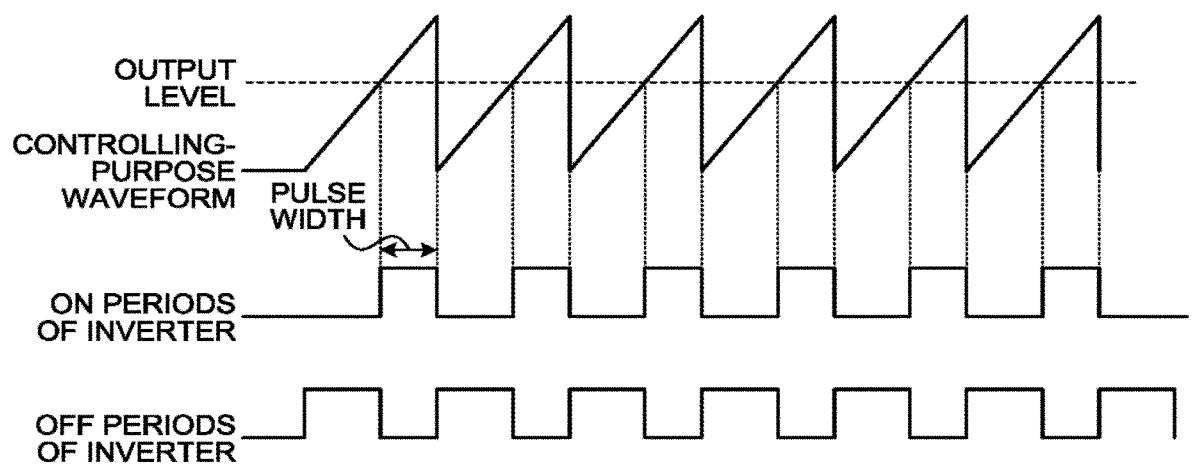
FIG. 4 is a drawing for explaining Pulse Width Modulation (PWM) control exercised by a PWM circuit.
Figure 5:
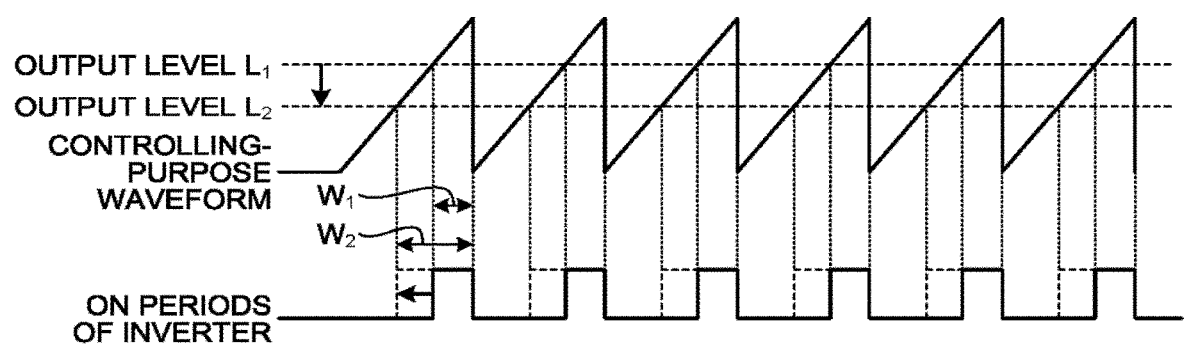
FIG. 5 is another drawing for explaining the PWM control exercised by the PWM circuit.

Next, the PWM control exercised by the PWM circuit 110 will be explained, with reference to FIGS. 4 to 6. FIGS. 4 to 6 are drawings for explaining the PWM control exercised by the PWM circuit 110. FIGS. 4 and 5 illustrate relevance between controlling-purpose signals used for exercising the PWM control and inverter ON periods. Further, FIG. 6 illustrates changes in the pulse width (the ON periods) (the horizontal axis) corresponding to an inverter current (the vertical axis).

As illustrated in FIG. 4, for example, the PWM circuit 110 generates a pulse signal having a pulse width that can achieve a desired output level, by using a carrier wave having a sawtooth waveform as a controlling-purpose waveform. More specifically, when the output level of the inverter circuit 112 becomes higher, the PWM circuit 110 makes the pulse width smaller. In contrast, when the output level of the inverter circuit 112 becomes lower, the PWM circuit 110 makes the pulse width larger. Further, to turn off the inverter circuit 112, the PWM circuit 110 generates a pulse signal having a phase opposite of the phase of the pulse signal corresponding to the inverter ON periods. The pulse signal having the opposite phase corresponds to inverter OFF time periods (hereinafter, "OFF periods").

Further, by using the two generated pulse signals, the PWM circuit 110 controls the ON/OFF state of the two pairs made up of the IGBTs 112A, 112B, 112C, and 112D described above. For example, the PWM circuit 110 outputs the two generated pulse signals to the IGBT driving circuit 111. The IGBT driving circuit 111 switches the two pairs on and off, with the timing indicated by each of the two pulse signals received from the PWM circuit 110.

In one example, the IGBT driving circuit 111 switches pair A (the IGBT 112A and the IGBT 112D) on and off with the timing based on the pulse signal corresponding to the inverter ON periods. In contrast, the IGBT driving circuit 111 switches pair B (the IGBT 112B and the IGBT 112C) on and off with the timing based on the pulse signal corresponding to the inverter OFF periods. With these arrangements, the inverter circuit 112 is able to supply the alternating-current voltage to the high voltage transformer 113A, as described above.

In this situation, when the inverter starts operating, the high-voltage output voltage increases from 0 V and eventually reaches a target voltage value. At that time, the ON periods (the pulse widths) of the inverter circuit become smaller, as the output level approaches the target voltage value. Further, when the output level has reached the target value, the ON periods (the pulse widths) of the inverter circuit become constant. In this situation, when the X-ray condition and the power supply voltage are constant, while there is no change in the state of the IGBTs 112A, 112B, 112C, and 112D, the pulse width that is output from the PWM circuit 110 does not change from the previous state. However, when the IGBTs 112A, 112B, 112C, and 112D become deteriorated and the ON resistance increases, the inverter current decreases, and also, the output voltage becomes lower. Accordingly, even the X-ray condition and the power supply condition are the same, the pulse width that is output from the PWM circuit becomes larger than the occurrence of deterioration.

More specifically, as illustrated in FIG. 5, even when the X-ray condition and the power supply condition are the same, the output level may decrease, in some situations, from $L_1$ to $L_2$ due to a decrease in the inverter current. In those situations, the PWM circuit 110 keeps the output voltage supplied to the X-ray tube 12 at a constant level, by extending the pulse width from a pulse width $W_1$ to a pulse width $W_2$, in accordance with the decrease in the output level. In other words, as illustrated in the top and the bottom sections of FIG. 6, the PWM circuit 110 controls the ON periods of the inverter circuit 112 so as to keep the area size of the regions indicated with the hatching constant, in accordance with the decrease in the inverter current.

In this situation, when the X-ray condition and the power supply voltage are constant, the decrease in the inverter current is caused by the deterioration (the increase in the ON resistance) of the power device (the IGBTs 112A, 112B, 112C, and 112D). Accordingly, when the ON period of the inverter circuit 112 becomes longer while the X-ray condition and the power supply voltage are the same, it is conjectured that the power device is getting deteriorated. To cope with this situation, the X-ray diagnosis apparatus 100 according to the present embodiment is configured to assess the product life of the power device by using changes in the pulse widths output from the PWM circuit 110.

Returning to the description of FIG. 2, the product life assessing circuit 115 is an electronic circuit configured to assess whether or not an ON period of the power device has exceeded a threshold value. For example, the threshold value is set to a value (a tolerated value) smaller than the ON period value that has a possibility of having the inverter circuit 112 damaged while a constant X-ray condition and a constant power supply voltage level are being used. The threshold value is stored in advance in a memory provided in the product life assessing circuit 115. The product life assessing circuit 115 is an example of the assessing circuit.

A process performed by the product life assessing circuit 115 according to the first embodiment will be explained with reference to FIGS. 7 and 8. FIGS. 7 and 8 are drawings for explaining the process performed by the product life assessing circuit 115 according to the first embodiment.

FIG. 7 illustrates threshold values for the ON periods of the power device that are set in correspondence with various types of X-ray conditions. For example, the threshold values illustrated in FIG. 7 are set by an installing person (a manufacturer, a designer, or the like) when the product life assessing circuit 115 is installed in the X-ray diagnosis apparatus 100. As illustrated in FIG. 7, the product life assessing circuit 115 is set with a plurality of threshold values in correspondence with a plurality of X-ray tube voltage values and a plurality of X-ray tube current values. More specifically, when the X-ray tube voltage is $V_1$ and the X-ray tube current is $A_1$, a threshold value $Th_1$ is set. When the X-ray tube voltage is $V_2$ and the X-ray tube current is $A_2$, a threshold value $Th_2$ is set. When the X-ray tube voltage is $V_3$ and the X-ray tube current is $A_3$, a threshold value $Th_3$ is set. When the X-ray tube voltage is $V_4$ and the X-ray tube current is $A_4$, a threshold value $Th_4$ is set. The situation illustrated in FIG. 7 is merely an example, and possible embodiments are not limited to the example illustrated in FIG. 7.

FIG. 8 illustrates a fluctuation in the output level after the power device is installed. FIG. 8 illustrates an example in which the X-ray tube voltage $V_1$ and the X-ray tube current $A_2$ are set as an X-ray condition. In other words, under the X-ray condition illustrated in FIG. 8, the product life assessing circuit 115 performs a product life assessing process on the power device by using the threshold value $Th_3$ presented in FIG. 7.

For example, immediately after the X-ray high voltage generator is installed, an output level $L_3$ is exhibited as illustrated in the top section of FIG. 8. In this situation, the pulse width controlled in accordance with this output level is $W_1$. In that situation, the product life assessing circuit 115 compares the pulse width $W_1$ with the threshold value $Th_3$. After that, because "$W_1<Th_3$" is satisfied, the product life assessing circuit 115 determines that the product life of the power device is not expiring and further outputs information indicating that the product life is not expiring to the processing circuitry 21. In one example, the product life assessing circuit 115 outputs an assessment result indicating that the pulse width is smaller than the threshold value to the processing circuitry 21.

In contrast, when a certain period of time has elapsed since the installation of the power device, an output level $L_4$, which is smaller than the output level $L_3$, may be exhibited, even when the X-ray condition is the same as the X-ray condition (the X-ray tube voltage $V_1$ and the X-ray tube current $A_2$) presented in the top section of FIG. 8, as illustrated in the bottom section of FIG. 8. In this situation, the pulse width controlled in accordance with this output level is $W_2$. In that situation, the product life assessing circuit 115 compares the pulse width $W_2$ with the threshold value $Th_3$. Further, because "$W_2>Th_3$" is satisfied, the product life assessing circuit 115 determines that the product life of the power device is expiring and further outputs information indicating that the product life is expiring to the processing circuitry 21. In one example, the product life assessing circuit 115 outputs an assessment result indicating that the pulse width is larger than the threshold value to the processing circuitry 21.

In this manner, the product life assessing circuit 115 assesses the product life of the power device (the IGBTs 112A, 112B, 112C, and 112D). In this situation, the product life assessing circuit 115 may store therein a plurality of threshold values corresponding to sets each made up of an X-ray condition of the X-rays and the power supply voltage of the power supply 5. In that situation, the product life assessing circuit 115 makes a comparison with the ON period, by using one of the threshold values corresponding to the set made up of the X-ray condition and the power supply voltage. Further, when the pulse width $W_1$ is smaller than the threshold value Th, the product life assessing circuit 115 does not need to output an assessment result to the processing circuitry 21.

Further, the processing circuitry 21 provides a notification about the assessment result obtained by the product life assessing circuit 115. For example, when having received, from the product life assessing circuit 115, an assessment result indicating that the pulse width is larger than the threshold value, the processing circuitry 21 causes the display 23 to display a message indicating that the product life of the power device is expiring (or a message indicating that replacing the power device is recommended). On the contrary, when having received, from the product life assessing circuit 115, an assessment result indicating that the pulse width is smaller than the threshold value, the processing circuitry 21 does not provide the notification.

The function of providing the notification about the assessment result (a notifying function) does not necessarily have to be realized with the abovementioned message but may be realized by using a sound (a buzzer) or light (a lamp). Further, in the description above, the example in which the processing circuitry 21 is provided with the notifying function is explained. However, the product life assessing circuit 115 or the X-ray high voltage generator 11 may be provided with the notifying function. In that situation, the product life assessing circuit 115 or the X-ray high voltage generator 11 includes a circuit (which may be referred to as a notifying unit or an output controlling unit) for executing the notifying function.

In other words, it is possible to realize the function (the assessing function) of the product life assessing circuit 115 and the notifying function, as processing circuitry configured to output information about the product life of the power device on the basis of the ON periods. That is to say, the assessing function and the notifying function may be executed by a single processor. Alternatively, the assessing function and the notifying function may be executed by individual processors. These processors may each be installed in an arbitrary position in the X-ray high voltage generator 11 or the X-ray diagnosis apparatus 100.

Further, when having received, from the product life assessing circuit 115, an assessment result indicating that the pulse width is smaller than the threshold value, the processing circuitry 21 may cause the display 23 to display a message indicating that the product life of the power device is not expiring.

As explained above, in the X-ray diagnosis apparatus 100 according to the first embodiment, the inverter circuit 112 is configured to control the output voltage to be output to the X-ray tube 12. Further, the IGBTs 112A, 112B, 112C, and 112D are provided for the inverter circuit 112 and are configured to perform the switching processes to control the output voltage. Further, the PWM circuit 110 is configured to control the switching processes performed by the IGBTs 112A, 112B, 112C, and 112D on the basis of the ON periods, in accordance with the output voltage. Further, the product life assessing circuit 115 is configured to assess whether or not an ON period exceeds the threshold value. With these arrangements, the X-ray diagnosis apparatus 100 according to the first embodiment is able to properly assess the product life of the IGBTs 112A, 112B, 112C, and 112D.

Accordingly, the operator of the X-ray diagnosis apparatus 100 is able to learn the expiration of the product life of the power device, before the power device is damaged. Consequently, the operator is able to address the situation by replacing the power device, for example, before the power device is damaged due to the expiration of the product life thereof. It is therefore possible to avoid the situations where an image taking process is disrupted or where the patient is affected.

In the first embodiment above, the IGBTs 112A, 112B, 112C, and 112D are used as an example of the power device; however, possible embodiments are not limited to this example. For instance, it is possible to realize the embodiment described above when another type of power device such as a Metal-Oxide-Semiconductor Field-Effect Transistor (MOS-FET) or the like is applied.

Further, the specifics of the drawings referred to in the first embodiment are not necessarily limited to those in the drawings. For instance, the configuration of the X-ray high voltage generator 11 and the specifics of the PWM control explained in the first embodiment are merely examples. It is acceptable to modify the configuration and the specifics as appropriate, so long as the contents of the processes performed by the product life assessing circuit 115 are not affected. For example, with reference to FIG. 2, the example is explained in which the product life assessing circuit 115 obtains the ON period in the stage subsequent to the PWM circuit 110; however, another arrangement is also acceptable in which the PWM circuit 110 obtains the ON period in the stage subsequent to the IGBT driving circuit 111.

Second Embodiment

In the first embodiment, the example is explained in which the X-ray condition and the power supply voltage, which are factors that affect the inverter current, are constant; however, possible embodiments are not limited to this example. For instance, the X-ray diagnosis apparatus 100 is capable of setting an appropriate threshold value by correcting the threshold value in accordance with changes in the factors that affect the inverter current.

Figure 9:
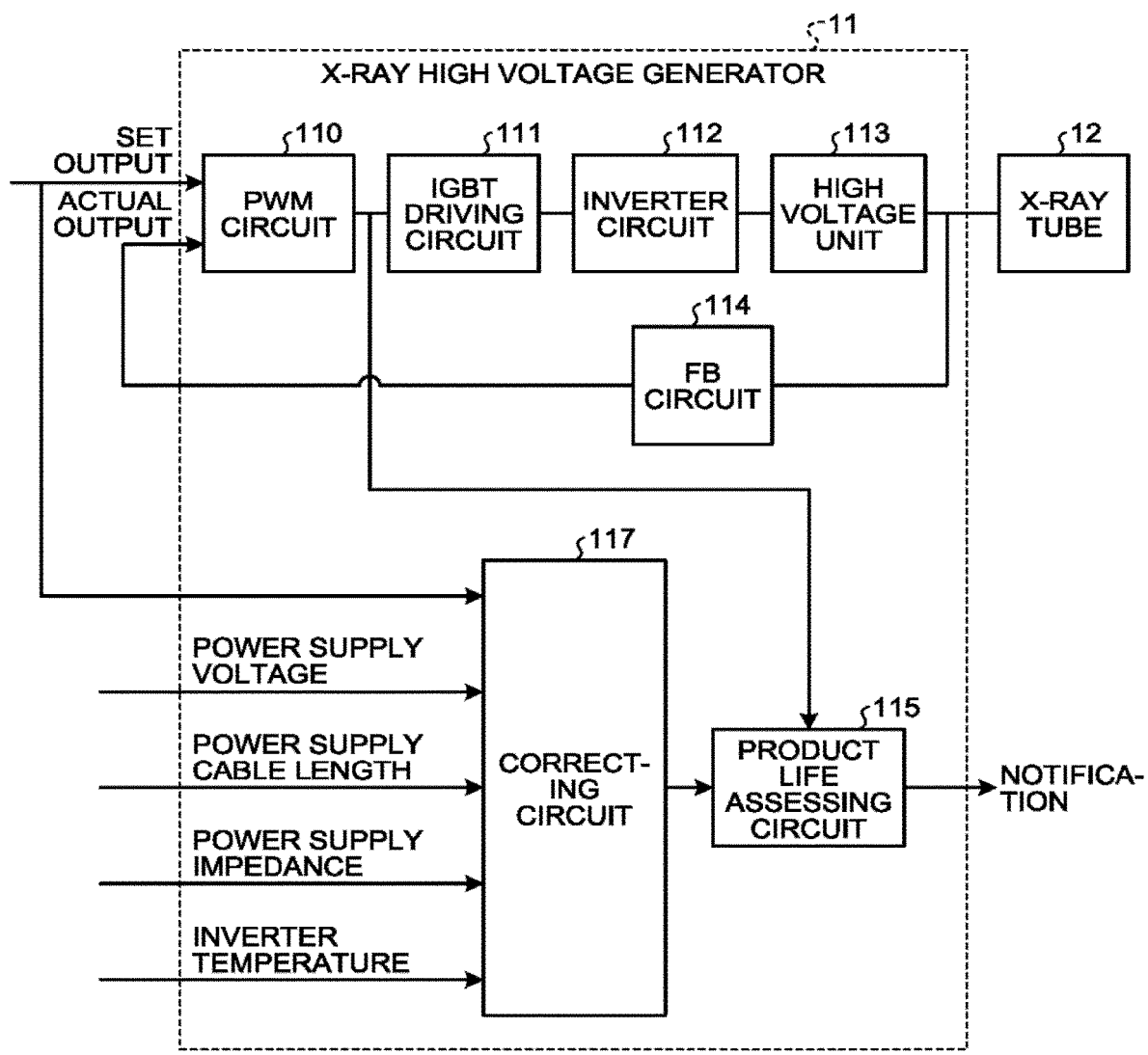
FIG. 9 is a block diagram illustrating an exemplary configuration of an X-ray diagnosis apparatus according to a second embodiment.

An exemplary configuration of the X-ray diagnosis apparatus 100 according to a second embodiment will be explained with reference to FIG. 9. FIG. 9 is a block diagram illustrating the exemplary configuration of the X-ray diagnosis apparatus 100 according to the second embodiment. The X-ray diagnosis apparatus 100 according to the second embodiment has a configuration similar to that of the X-ray diagnosis apparatus 100 illustrated in FIG. 1 and is different in that the X-ray high voltage generator 11 further includes a correcting circuit 117. Thus, the second embodiment will be explained while a focus is place on the difference from the first embodiment. Some of the constituent elements having the same functions as those explained in the first embodiment will be referred to by using the same reference characters as those in FIG. 1, and the explanations thereof will be omitted.

The correcting circuit 117 is configured to correct the threshold value on the basis of one or more factors that affect the inverter current supplied to the inverter circuit 112. For example, as the factors that affect the inverter current, the correcting circuit 117 corrects the threshold value on the basis of at least one selected from among: the power supply voltage of the power supply 5 connected to the X-ray high voltage generator 11, the length of the power supply cable, the power supply impedance, and the temperature of the inverter circuit 112.

Figure 10:
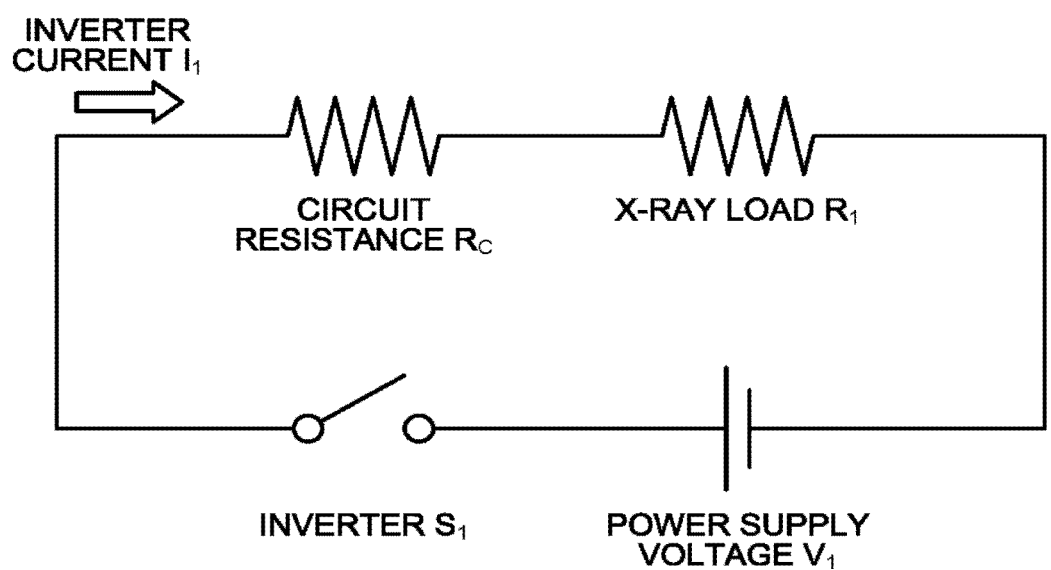
FIG. 10 is a drawing for explaining a process performed by a correcting circuit according to the second embodiment.

In other words, even under the same X-ray condition, it is considered that the magnitude of the inverter current per pulse in the X-ray high voltage generator 11 varies due to changes not only in the pulse width, but also in the power supply voltage on that day, the length of the power supply cable extending from a switchboard, the power supply impedance, and the inverter circuit resistance caused by the temperature of the inverter, and the like. To further explain, an equivalent circuit is illustrated (in FIG. 10) which simply expresses the power supply voltage as a direct-current power supply $V_0$; an X-ray load based on the X-ray condition as a resistance $R_1$; the circuit resistance caused by the length of the power supply cable and the power supply impedance as a resistance $R_C$; the inverter current as a current $I_1$; and the inverter as a switch $S_1$. FIG. 10 is a drawing for explaining a process performed by the correcting circuit 117 according to the second embodiment.

In FIG. 10, for example, when the power supply voltage has changed from $V_0$ to $V_1$, when there is no change in the X-ray condition while the X-ray load remains to be $R_1$, it is possible to correct the threshold value by using Expression (1) presented below. The threshold value $Th_0$ is the threshold value before the correction, whereas the threshold value $Th_1$ is the threshold value after the correction.

$$Th_1 = Th_0 \times \frac{V_1}{V_0} \quad (1)$$

In this situation, by using the circuit equations presented below (Expressions (2) and (3)), it is possible to calculate the circuit resistance $R_C$ by measuring the power supply voltage $V_1$ and the inverter current $I_1$ corresponding to the X-ray load $R_1$, at the time of installation of the device.

$$V_1 = (R_c + R_1) \times I_1 \quad (2)$$

$$R_c = \frac{V_1}{I_1} - R_1 \quad (3)$$

As explained above, the correcting circuit 117 according to the second embodiment is able to correct the threshold value on the basis of the one or more factors that affect the inverter current supplied to the inverter circuit 112. With this arrangement, the X-ray diagnosis apparatus 100 is able to assess the product life of the IGBTs 112A, 112B, 112C, and 112D more properly.

Other Embodiments

The present disclosure may be carried out in various different modes other than those explained in the above embodiments.

Setting a Threshold Value on the Basis of an ON Period at the Time of Installation For example, the product life assessing circuit 115 may set a threshold value on the basis of an ON period of the power device measured at the time of the installation of the X-ray high voltage generator 11.

For example, an X-ray output adjusting process is always performed on X-ray power supplies at the time of installation of the device. Among the factors that affect the inverter current mentioned above, the length of the power supply cable and the power supply impedance are confirmed when the device has been installed. For this reason, by setting a threshold value (a tolerated value) while using the pulse width (an original pulse width) resulting from the X-ray output adjusting process performed at the time of installation as a reference, it is possible to easily set an accurate threshold value.

Accordingly, the pulse width $W_1$ resulting from the X-ray output adjusting process performed at the time of installation shall be stored together with the power supply voltage $V_1$ and the X-ray condition $R_1$. Further, for example, with respect to the original pulse width $W_1$, the product life assessing circuit 115 is set, in advance, with information indicating that "a value with an additional 20% is used as a threshold value (a tolerated value) for assessing expiration of the product life".

Further, the product life assessing circuit 115 monitors the actual pulse width W corresponding to the same X-ray condition $R_1$, while using "$W_1 \times 1.2$" as the threshold value Th. After that, when the actual pulse width W exceeds the value "$W_1 \times 1.2$", the product life assessing circuit 115 determines that the product life of the power device is expiring. With this arrangement, without the need to prepare a threshold value in advance, it is possible to easily set the accurate threshold value by using the ON period of the power device measured at the time of installation of the X-ray high voltage generator 11.

A Process of Assessing the Product Life During a Warm-Up Operation

Further, for example, the product life assessing circuit 115 may assess whether or not an ON period measured during a warm-up operation of the X-ray high voltage generator 11 exceeds a threshold value.

For example, for the X-ray diagnosis apparatus 100, it is a common practice to heat the X-ray tube 12 by performing a warm-up operation before the apparatus starts being used (every morning). Because the X-ray condition of the output is fixed during the warm-up operation, it is possible to assess the product life under a constant X-ray condition by bringing the product life assessing function for the power device into operation during the warm-up operation. This arrangement is expected to improve the level of precision of the product life assessing process. Further, because it is possible to assess the product life under the limited X-ray condition, there is no need to store a plurality of threshold values. It is therefore possible to reduce the use of infrastructure such as memory.

An X-Ray Imaging Apparatus

In the embodiments described above, the example is explained in which the X-ray high voltage generator 11 is applied to the X-ray diagnosis apparatus 100; however, possible embodiments are not limited to this example. For instance, the X-ray high voltage generator 11 is applicable to any X-ray imaging apparatus having the X-ray tube 12 installed therein. Examples of the X-ray imaging apparatus include X-ray CT apparatuses besides the X-ray diagnosis apparatus 100.

More specifically, the X-ray imaging apparatus includes the inverter circuit 112, the power device, the PWM circuit 110, the product life assessing circuit 115, and a notifying unit. The inverter circuit 112 is configured to control the output voltage to be output to the X-ray tube 12 that generates X-rays. The power device is provided for the inverter circuit 112 and is configured to perform a switching process to control the output voltage. In accordance with the output voltage, the PWM circuit 110 is configured to control the switching process performed by the power device on the basis of the ON periods. The product life assessing circuit 115 is configured to assess whether or not an ON period exceeds the threshold value. The notifying unit is configured to provide a notification about the result of the assessment made by the assessing circuit.

A Product Life Assessing Circuit

Further, in the embodiments described above, the example is explained in which the X-ray high voltage generator 11 is included, in advance, in the X-ray imaging apparatus; however, possible embodiments are not limited to this example. For instance, it is also possible to realize the X-ray high voltage generator 11 by incorporating the product life assessing circuit 115 into an existing X-ray high voltage generator. In other words, it is also possible to realize the X-ray high voltage generator 11 of the present embodiments, by additionally incorporating the product life assessing circuit 115 into an X-ray high voltage generator included in an X-ray imaging apparatus that has already been shipped as a product.

That is to say, the product life assessing circuit 115 is configured to assess whether or not the ON period exceeds the threshold value, with respect to the power device provided in the inverter circuit 112 on which feedback control is exercised in accordance with the output voltage for the purpose of controlling the output voltage to be output to the X-ray tube 12. In other words, the product life assessing circuit 115 is configured to assess whether or not the ON period exceeds the threshold value with respect to the power device provided in the inverter circuit 112 for controlling the voltage by exercising the PWM control.

Fluctuation of the Output

Further, generally speaking, outputs (the output voltage or the output current) of power supply devices (e.g., the X-ray high voltage generator 11) may fluctuate in some situations. For example, it is known that the output significantly fluctuates when a power supply device is started up. When the output fluctuates significantly in such situations, the ON period also fluctuates significantly. For this reason, it is desirable to configure the product life assessing circuit 115 described in the above embodiments so as to assess whether or not an ON period measured after the output voltage (or the output current) becomes stable exceeds the threshold value. For example, it is desirable to configure the product life assessing circuit 115 so as not to perform the product life assessing process on the power device for a predetermined time period since the X-ray high voltage generator 11 is started up. For example, the "predetermined time period" may be set in advance on the basis of how much time is required by the start-up.

In this regard, the situation in which the output is stable denotes a situation in which the extents of fluctuation of the outputs that are repeatedly yielded over the course of time are substantially constant. For this reason, another arrangement is also acceptable in which the product life assessing process is performed on the power device after judging whether or not the output is stable. For example, when the judgment as to whether the output is stable or not is made on the operator side, the product life assessing circuit 115 is configured to perform the product life assessing process on the power device, according to timing designated by the operator. In contrast, when the judgment as to whether the output is stable or not is automatically performed, for example, the product life assessing circuit 115 performs the product life assessing process on the power device when the fluctuation of the output is smaller than a threshold value.

Utilizing an Average Value of ON Periods

In the embodiments described above, the example is explained in which the product life assessing process is performed on the power device by using the ON period at a certain point in time; however, the possible embodiments are not limited to this example. For instance, the product life assessing circuit 115 may also be configured to calculate an average value of a plurality of ON periods and to assess whether or not the calculated average value exceeds a threshold value. In this situation, for example, the plurality of ON periods may be a plurality of ON periods that are consecutively sampled during a certain period of time or may be a plurality of ON periods that are intermittently sampled in multiple sessions during one day. It should be noted, however, the ON periods used for calculating the average value shall be sampled while the output is stable.

A Medical Power Supply Device

The embodiments described above are applicable not only to X-ray imaging apparatuses, but also to a power supply device (a gradient power supply) that supplies a current to a gradient coil in a Magnetic Resonance Imaging (MRI) apparatus, for example. In this situation, because such a gradient power supply is configured to control the ON periods on the basis of the output current (the current value), it is desirable to perform the product life assessing process on the power device on the basis of the output current.

In other words, the embodiments described above are applicable to X-ray imaging apparatuses and to medical power supply devices including a gradient power supply. An example of the medical power supply devices includes an inverter circuit, a power device, a PWM circuit, and processing circuitry. The inverter circuit is configured to control either the output voltage or the output current. The power device is provided for the inverter circuit and is configured to perform the switching process to control either the output voltage or the output current. The PWM circuit is configured to control the ON periods of the switching process performed by the power device, in accordance with either the output voltage or the output current. The processing circuitry is configured to output the information about the product life of the power device on the basis of an ON period. With these arrangements, the medical power supply device is able to properly assess the product life of the power device.

With regard to the processes explained in the embodiments described above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments explained above, it is possible to properly assess the product life of the power device.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray high voltage generator comprising:
    an inverter circuit configured to control output voltage to be output to an X-ray tube configured to generate an X-ray;
    a power device that is provided for the inverter circuit and is configured to perform a switching process to control the output voltage;
    a Pulse Width Modulation (PWM) circuit configured to control the switching process performed by the power device on a basis of an ON time period in accordance with the output voltage; and
    processing circuitry configured to output information about a product life of the power device on a basis of the ON time period.

2. The X-ray high voltage generator according to claim 1, wherein the processing circuitry assesses whether or not the ON time period exceeds a threshold value and provides a notification about a result of the assessment.

3. The X-ray high voltage generator according to claim 2, further comprising a correcting circuit configured to correct the threshold value on a basis of a factor that affects an inverter current supplied to the inverter circuit.

4. The X-ray high voltage generator according to claim 3, wherein the correcting circuit corrects the threshold value on a basis of at least one selected, as the factor, from among: power supply voltage of a power supply connected to the X-ray high voltage generator, a length of a power supply cable, a power supply impedance level, and a temperature of the inverter circuit.

5. The X-ray high voltage generator according to claim 2, wherein the processing circuitry sets the threshold value on a basis of the ON time period of the power device measured at a time of installation of the X-ray high voltage generator.

6. The X-ray high voltage generator according to claim 2, wherein the processing circuitry assesses whether or not the ON time period during a warm-up operation of the X-ray high voltage generator exceeds the threshold value.

7. The X-ray high voltage generator according to claim 2, wherein the processing circuitry assesses whether or not the ON time period measured after the output voltage becomes stable exceeds the threshold value.

8. The X-ray high voltage generator according to claim 2, wherein the processing circuitry calculates an average value of a plurality of ON time periods and assesses whether or not the calculated average value exceeds the threshold value.

9. An X-ray imaging apparatus comprising:
    an inverter circuit configured to control output voltage to be output to an X-ray tube configured to generate an X-ray;
    a power device that is provided for the inverter circuit and is configured to perform a switching process to control the output voltage;
    a Pulse Width Modulation (PWM) circuit configured to control the switching process performed by the power device on the basis of an ON time period in accordance with the output voltage; and processing circuitry configured to output information about a product life of the power device on a basis of the ON time period.

10. An assessing circuit configured to assess whether or not an ON time period of a power device provided in an inverter circuit used for controlling voltage by exercising Pulse Width Modulation (PWM) control exceeds a threshold value.

11. A medical power supply device comprising:
- an inverter circuit configured to control either output voltage or an output current;
- a power device that is provided for the inverter circuit and is configured to perform a switching process to control either the output voltage or the output current;
- a Pulse Width Modulation (PWM) circuit configured to control an ON time period of the switching process performed by the power device in accordance with either the output voltage or the output current; and
- processing circuitry configured to output information about a product life of the power device on a basis of the ON time period.

* * * * *